United States Patent [19]

Land

[11] 4,279,150
[45] Jul. 21, 1981

[54] APPARATUS FOR DETERMINING VAPOR CONTENT OF A GAS/VAPOR MIXTURE

[75] Inventor: Thomas Land, Grindleford, England

[73] Assignee: Land Pyrometers Limited, Dronfield, England

[21] Appl. No.: 108,002

[22] Filed: Dec. 28, 1979

[30] Foreign Application Priority Data

Jan. 11, 1979 [GB] United Kingdom ............... 00837/79

[51] Int. Cl.³ ........................................... G01N 25/64
[52] U.S. Cl. ............................... 73/338; 73/338.6
[58] Field of Search .................. 73/338, 338.6, 77, 29

[56] References Cited

U.S. PATENT DOCUMENTS

| 2,623,391 | 12/1952 | Malecki | 73/338 |
| 3,196,683 | 7/1965 | Gross | 73/338 |
| 3,253,465 | 5/1966 | Miller | 73/338 X |
| 3,515,001 | 6/1970 | Greenspan et al. | 73/338.6 |
| 3,712,140 | 1/1973 | Grasso et al. | 73/338 |
| 3,890,828 | 6/1975 | Pleva | 73/29 |

FOREIGN PATENT DOCUMENTS 2343249  9/1977  France .

Primary Examiner—Gerald Goldberg
Assistant Examiner—Joseph W. Roskos
Attorney, Agent, or Firm—Sigalos & Levine

[57] ABSTRACT

Apparatus for determining the vapor content of a gas/vapor mixture comprises two temperature sensing devices. One of the devices measures the temperature of a liquid evaporating from a liquid saturated wick in contact with the device. The other temperature sensing device measures the temperature of the gas/vapor mixture in which it is immersed. A cooling device is provided for condensing some of the vapor from the gas/vapor mixture to maintain a liquid supply for the wick.

21 Claims, 4 Drawing Figures

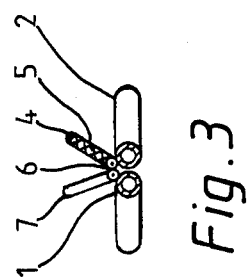
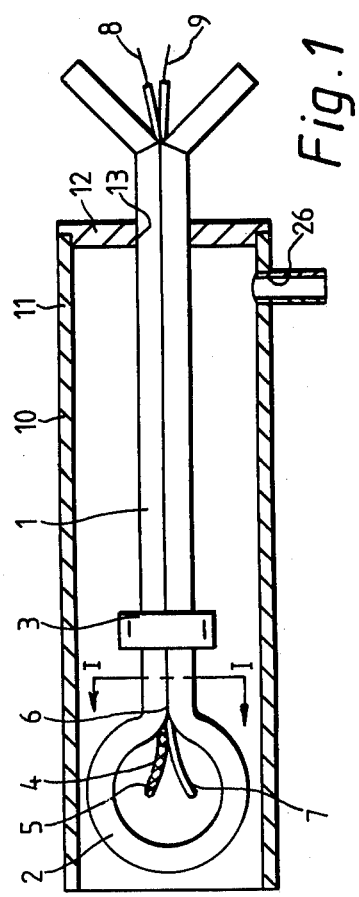
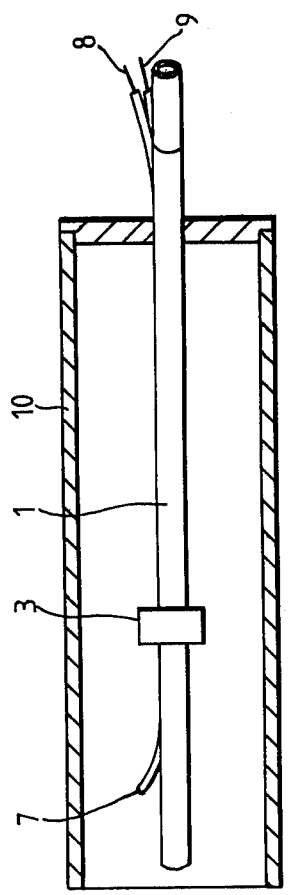

APPARATUS FOR DETERMINING VAPOR CONTENT OF A GAS/VAPOR MIXTURE

The invention relates to apparatus for determining the vapour content of a gas/vapour mixture.

Such apparatus, hereinafter referred to as of the kind described, comprises two temperature sensing devices one of which measures the temperature of a liquid evaporating from a liquid saturated wick in contact with the device, and the other of which measures the temperature of the gas/vapour mixture in which it is immersed.

In one well known method for determining relative humidity, the two temperature sensing devices are provided by mercury in glass thermometers one of which has its bulb covered with a sleeve of a suitable textile material which dips into a small reservoir of distilled water and acts as a wick. The water is drawn up the wick by capillary action so that the bulb of the thermometer is always surrounded by a water surface exposed to the gas. This "wet" bulb is cooled by the evaporation of the water. The temperature difference between the wet and the "dry" bulbs is called the depression of the web bulb temperature. The relationship between the partial pressure (e) of water vapour in the gas, the vapour pressure (e') of water at the temperature of the wick, and the depression of the wet bulb temperature is usually given by the following equation:

$$e = e' - 6.66 \times 10^{-4} P(t - t')$$

where
P is the atmospheric pressure,
t is the gas temperature in degrees C, and
t' is the web bulb temperature in degrees C.

The relative humidity of the gas can then be found by knowing the wet and dry bulb temperatures, since the water content of the gas by volume is very simply related to the partial pressure of the water vapour in the gas. Because the rate of evaporation and the rate of heat transfer depend on the same process of molecular diffusion the same equation can be used over a wide range of gas velocities.

The wet and dry bulb thermometer is normally used for spot checks on atmospheric humidity. The unit, comprising the two thermometers and the distilled water reservoir, is swung gently to and fro in the air and the two temperatures are noted. Problems arise when an attempt is made to use this unit to measure gas humidity on a continuous basis in an industrial process. It is found difficult to provide a continuous supply of distilled water.

According to the present invention, apparatus of the kind described, for determining the vapour content of a gas/vapour mixture is characterised by the provision of a cooling device for condensing some of the vapour from the gas/vapour mixture to maintain a liquid supply for the wick.

Thus by condensing out, for example the water vapour, already present in the gas, the need for a separate water supply for the wick is avoided.

The cooling device may comprise a reservoir for collection of the condensed vapour and in which part of the wick is located.

The cooling device may be provided by a jacket surrounding part of the wick and through which a cooling medium is circulated. Preferably, the cooling device comprises an air or water cooled surface. Alternatively, the cooling device may comprise a thermoelectrically cooled surface.

The temperature sensing devices may be provided by mercury in glass thermometers, conventional thermocouples, resistance thermometers, or other conventional devices.

It is particularly convenient if the wick is made of a mineral fibre textile capable of withstanding exposure to hot gases since this extends the range of temperature over which measurements may be made.

Preferably, the apparatus further comprises means connected to the temperature sensing devices for calculating the concentration of vapour in the gas/vapour mixture.

It will be appreciated that since a separate source of liquid for saturating the wick is not required, the apparatus is particularly useful for monitoring continuously the vapour content of a gas/vapour mixture. Further, the apparatus will be most useful in measuring water content in warm environments where drying is taking place.

Two examples of an apparatus constructed in accordance with the invention are illustrated in the accompanying drawings, in which:

FIG. 1 is a diagrammatic part sectional view of one example of the apparatus inserted in a sampling chamber;

FIG. 2 is a diagrammatic side elevation of the example shown in FIG. 1;

FIG. 3 is a section taken on the line I—I in FIG. 1; and,

Figure 4:
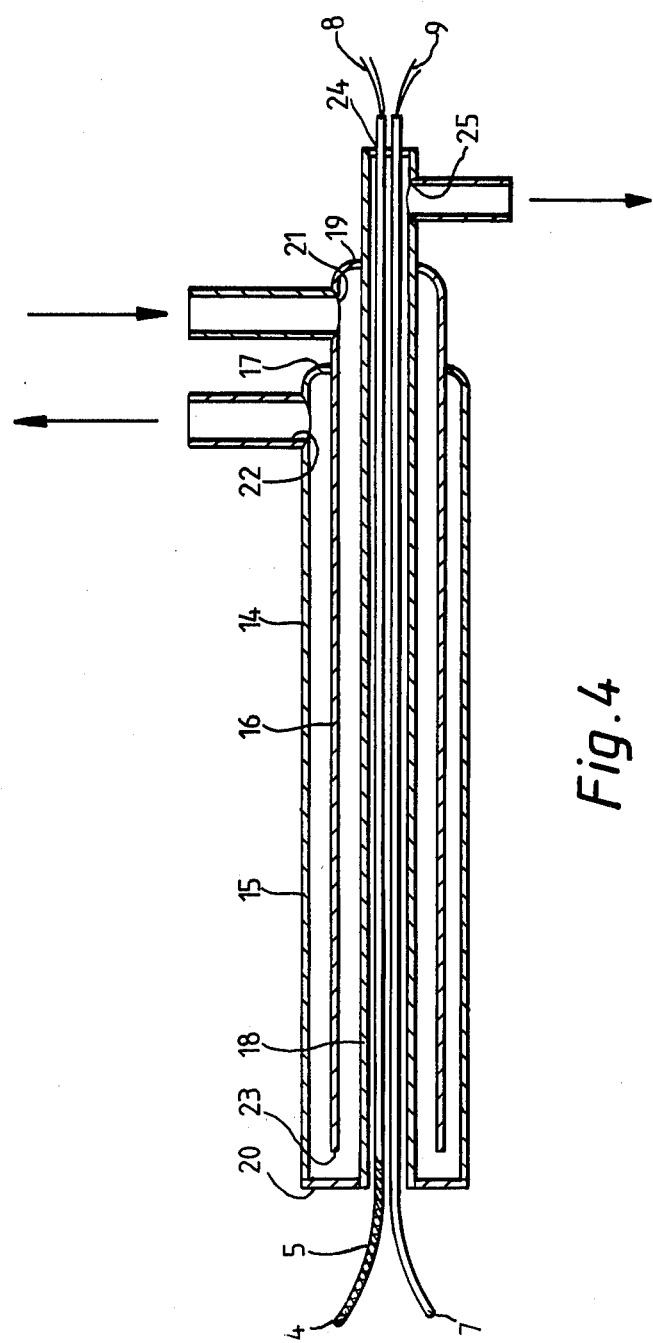
FIG. 4 is a diagrammatic part sectional view of a second example of the apparatus.

In the example illustrated in FIGS. 1 to 3, the cooling device is formed by a stainless steel tube 1 which is bent into a loop 2 at one end. The two arms of the tube 1 are held in contact with one another by a clamp 3.

A "wet" temperature sensing device is provided by a mineral insulated thermocouple 4 whose protection sheath is made of stainless steel. The thermocouple 4 is covered over a length of about 50 thermocouple diameters with a glass silk sleeving 5 which acts as a wick but is not subject to rotting or other corrosive effects that might be induced by the high temperature and moist conditions of the surrounding atmosphere. The thermocouple 4 is fitted into a crevice 6 between the two arms of the tube with the wick 5 also extending back into the crevice.

A "dry" temperature sensing device is, in this example, provided by a second mineral insulated thermocouple 7. This thermocouple 7 is also fitted into the crevice 6. Leads 8, 9 from the thermocouples 4, 7 respectively extend back along the length of the arms of the tube 1 and may be connected to a conventional device for converting signals from the thermocouples into temperature readings.

The apparatus is fitted into a sampling chamber 10. The sampling chamber 10 comprises a cylindrical casing 11 into one end of which is fitted a plug 12. The plug 12 is provided with an axial hole 13 which receives the two arms of the tube 1.

In use, the apparatus and sampling chamber 10 are inserted horizontally into a gas/vapour mixture where, for example, the vapour may be water vapour. Water is circulated around inside the tube 1 by a pump (not shown) to maintain the surface of the tube at a temperature below the dew point of the surrounding gas. The gas/vapour mixture is then drawn at a predetermined velocity into the sampling chamber and through an aperture 26 by a suction pump (not shown). Moisture will condense out of the gas/vapour mixture and collect in the crevice 6 to form a small reservoir of distilled water. A steady flow of water will then be taken up by the wick 5 from the reservoir by capillary action. As may be seen from FIGS. 2 and 3, the thermocouples 4,7 both slope slightly upward away from the crevice 6 to prevent any flow of water down the thermocouple under gravity.

The leads 8, 9 may, alternatively, be connected to an electronic circuit which can simulate the equation that relates the depression of the wet bulb temperature to the partial pressure of the water vapour in the gas (see above) in such a way that an output is provided which indicates the percentage of water vapour by volume in the hot moist gas.

A second example of the apparatus is illustrated in FIG. 4. The temperature sensing devices are similar to those shown in the first example and comprise a "wet" and a "dry" thermocouple 4, 7, the wet thermocouple being covered by a wick 5. In this case however, the cooling device is provided by a jacket 14 through which cooling medium, for example water, is pumped. The jacket 14 comprises an outer, cylindrical, tubular portion 15 and an intermediate, cylindrical, tubular portion 16. The portion 16 is fitted into an integral, radially extending end section 17 of the outer portion 15. An inner, cylindrical, tubular portion 18 is provided concentric with the portions 15, 16. The portion 18 is fitted into an integral, radially extending end section 19 of the portion 16. An annular plate 20 is fixed to the end of the portion 15 remote from the radially extending section 17, and to the adjacent end of the portion 18. Two apertures 21, 22 are provided in the portions 16, 15 respectively for permitting the introduction and withdrawal of cooling medium from the jacket 14. Cooling medium enters through the aperture 21, passes between the cylindrical portions 16, 18, passes around an end 23 of the portion 16 adjacent to the plate 20, between the portions 15, 16 and out through the aperture 22. In this example the jacket 14 is made of stainless steel.

The thermocouples 4, 7 are positioned to project through a central aperture in the plate 20. The leads 8, 9 of the thermocouples 4, 7 extend through the inner portion 18 and out through a plug 24 which closes the end of the portion 18 remote from the plate 20. An aperture 25 is provided adjacent the plug 24 in the inner portion 18 through which the gas/vapour mixture may be drawn by suction.

In operation, the apparatus is inserted horizontally into a gas/vapour mixture and water or another cooling medium is circulated through the jacket 14, as previously described. The gas/vapour mixture is then drawn at a predetermined velocity through the inner portion 18 and the aperture 25 by a suction pump (not shown). Due to the low temperature of the inner portion 18, vapour will condense out of the gas/vapour mixture to supply the wick 5. Preferably the apparatus slopes slightly towards the thermocouples 4,7 so that condensed vapour will collect in the lowermost section of the portion 18 and form a reservoir to feed the wick 5. As in the previous example, the leads 8,9 may be connected to a device for displaying the temperatures sensed or to convert the temperature readings to provide a direct output of the percentage of vapour by colume in the gas/vapour mixture.

One example of the use of this apparatus is in the measurement of the water content of the hot air in a drying hood of a paper making machine. It enables the operator to check that water is being removed from the paper at the desired rate so as to ensure that the proper drying procedure is taking place without unnecessary waste of heat.

I claim:

1. Apparatus for determining the vapour content of a gas/vapour mixture, said apparatus comprising two temperature sensing devices, one of said devices being adapted to measure the temperature of a gas/vapour mixture in which said device is immersed; a wick in contact with the other of said devices; a cooling device for condensing vapour from said gas/vapour mixture to maintain a liquid supply for said wick, said other temperature sensing device being adapted to measure the temperature of said liquid evaporating from said wick, said cooling device comprising a reservoir for collection of said condensed vapour and in which part of said wick in located, and a tube; said apparatus further comprising a sampling chamber in which said tube is mounted, means for circulating a cooling medium through said tube, and means for drawing the gas/vapour mixture through said sampling chamber so that vapour condenses out of said gas/vapour mixture onto a surface of said tube to form said reservoir, wherein two parts of said tube extend alongside and in contact with one another to form a V-shaped reservoir in which said condensed vapour collects.

2. Apparatus according to claim 1, wherein said temperature sensing devices are coupled to leads extending along said passage.

3. Apparatus according to claim 1, wherein said cooling device comprises an air cooled surface.

4. Apparatus according to claim 1, wherein said cooling device comprises a water cooled surface.

5. Apparatus according to claim 1, wherein said cooling device comprises a thermo-electrically cooled surface.

6. Apparatus according to claim 1, wherein at least one of said temperature sensing devices is a mercury in glass thermometer.

7. Apparatus according to claim 1, wherein at least one of said temperature sensing devices is a thermocouple.

8. Apparatus according to claim 1, wherein at least one of said temperature sensing devices is a resistance thermometer.

9. Apparatus according to claim 1, wherein said wick comprises a mineral fibre textile capable of withstanding exposure to hot gases.

10. Apparatus according to claim 1, further comprising means connected to said temperature sensing devices and adapted to calculate the concentration of vapour in the gas/vapour mixture.

11. Apparatus for determining the vapour content of a gas/vapour mixture, said apparatus comprising an elongate tubular housing having first and second ends, said housing being adapted to project into a gas/vapour mixture stream with said first end in said stream; a passage extending through said housing from said first end to said second end and through which a portion of said gas/vapour mixture is drawn; first and second temperature sensing devices mounted at said first end of said housing, said first device being adapted to sense the temperature of said gas/vapour mixture in which said first device is immersed; a wick in contact with said second device, said second device being adapted to sense the temperature of liquid evaporating from said wick; cooling means for circulating cooling medium within said housing from said second end of said housing to said first end and to return said cooling medium to said second end, for condensing vapour from said gas/vapour mixture portion passing through said passage; and a reservoir provided within said housing for collection of said condensed vapour and in which a part of said wick is located, whereby said cooling means is adapted to condense sufficient vapour to maintain saturation of said wick.

12. Apparatus according to claim 11, wherein said temperature sensing devices are coupled to leads extending along said passage.

13. Apparatus according to claim 11 or claim 12, wherein said cooling means comprises a tube, two parts of said tube extending alongside and in contact with one another to form a V-shaped reservoir in which said condensed vapour collects.

14. Apparatus according to claim 11 or claim 12, wherein said cooling means comprises a jacket adapted to circulate cooling medium there through, said jacket comprising an outer wall defined by said housing, and a tubular, inner wall surrounding said passage.

15. Apparatus according to claim 11, wherein said cooling device comprises an air cooled surface.

16. Apparatus according to claim 11, wherein said cooling device comprises a water cooled surface.

17. Apparatus according to claim 11, wherein at least one of said temperature sensing devices is a mercury in glass thermometer.

18. Apparatus according to claim 11, wherein at least one of said temperature sensing devices is a thermocouple.

19. Apparatus according to claim 11, wherein at least one of said temperature sensing device is a resistance thermometer.

20. Apparatus according to claim 11, wherein said wick comprises a mineral fibre textile capable of withstanding exposure to hot gases.

21. Apparatus according to claim 11, further comprising means connected to said temperature sensing devices and adapted to calculate the concentration of vapour in the gas/vapour mixture.

* * * * *